US00PP14025P39

(12) United States Plant Patent
Moser

(10) Patent No.: US PP14,025 P3
(45) Date of Patent: Jul. 29, 2003

(54) CHRYSANTHEMUM PLANT NAMED 'MOZA BN 01'

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 21 days.

(21) Appl. No.: 09/864,914

(22) Filed: May 24, 2001

(65) Prior Publication Data

US 2002/0188975 P1 Dec. 12, 2002

(51) Int. Cl.[7] ..... A01H 5/00

(52) U.S. Cl. ..... Plt./286

(58) Field of Search ..... Plt./286, 295, 296

*Primary Examiner*—Bruce R. Campell
*Assistant Examiner*—Anne Marie Grünberg
(74) *Attorney, Agent, or Firm*—Knobbe, Martens, Olson & Bear, LLP

(57) ABSTRACT

A new and distinct Chrysanthemum plant variety characterized by a daisy type inflorescence with many tightly held ray florets, consistent flowering response to short days, blooming consistently after 49 days of short day length, compact growth habit, and consistent natural season flowering habit during mid September.

1 Drawing Sheet

LATIN NAME OF THE GENUS AND SPECIES OF THE PLANT CLAIMED

*Chrysanthemum morifolium.*

VARIETY DENOMINATION

'MOZA BN 01'.

BACKGROUND OF THE INVENTION

The present invention relates to a new and distinct cultivar of Chrysanthemum plant, herein after referred to by the cultivar name 'MOZA BN 01'.

This new cultivar originated from hybridization of a female parent Chrysanthemum cultivar MZ 215-01 (unpatented in the United States, and undistributed commercially) with a male parent Chrysanthemum cultivar MZ 257-01 (unpatented in the United States, and undistributed commercially). The new cultivar was discovered by the inventor in November 1998.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'MOZA BN 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MOZA BN 01.' These characteristics in combination distinguish 'MOZA BN 01' as a new and distinct Chrysanthemum:

1. Daisy type inflorescence with many tightly held ray florets;

2. Consistent flowering response to short days, blooming consistently after 49 days of short day length;

3. Compact growth habit; and

4. Consistent natural season flowering habit during mid September.

Plants of the new cultivar are similar to plants of the female parent cultivar in most horticultural characteristics, however plants of the new cultivar differed from plants of the female parent cultivar in the following characteristics:

1. The new cultivar has different color ray florets;

2. The new cultivar is shorter;

3. The new cultivar has shorter internode length; and

4. The new cultivar has many more ray florets than the parent.

Plants of the new cultivar are similar to plants of the male parent cultivar in most horticultural characteristics, however plants of the new cultivar differed from plants of the male parent cultivar in the following characteristics:

1. The new cultivar has different color ray florets;

2. The new cultivar is taller; and

3. The new cultivar has a different type bloom.

BRIEF DESCRIPTION OF THE PHOTOGRAPHS

The photograph shows a plant of the new cultivar grown in a 4-inch container. A single cutting was propagated in the container. It was planted in mid-July and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants that were approximately 85 days old, which were grown in a commercial field in Oxnard, Calif. in the month of September 2000. The plants were grown from a rooted cutting given one pinch after 10 days from planting. There was no spray or disbud treatment given. The growing conditions range from 60° to 65° F. at night to 70° to 85° during the day. Measurements and numerical values represent averages of typical flowering types.

Botanical classification: *Chrysanthemum morifolium* cultivar 'MOZA BN 01'.
Commercial classification: Garden-type Chrysanthemum.
Parentage: Hybridization of female parent Chrysanthemum cultivar MZ 215-01 (unpatented in the United States) with a male parent Chrysanthemum cultivar MZ 257-01 (unpatented in the United States).
Comparison variety: Oriole U.S. Plant Pat. No. 10,181.

The new cultivar differs from Oriole in having bi-color ray florets, as opposed to Oriole's solid color ray florets, the new variety has more inflorescences per flowering branch, smaller diameter inflorescence, more ray florets and less disc florets.

Comparison variety: Grace U.S. Plant Pat. No. 7,642.

The new cultivar differs from Grace in having a later natural season bloom response, smaller diameter inflorescence, more inflorescence per flowering branch and more ray florets.

PROPAGATION

Time to rooting: 7 to 14 days at approximately 21° C.
Rooting habit: Fine, fibrous.

PLANT

Growth habit: Mounding herbaceous perennial.
Height: Approximately 19 cm.
Internode length: Approximately 2.2 cm.
Branching characteristics: Free Branching.
Length of lateral branches: Approximately 15 cm.
Number of leaves per lateral branch: Approximately 12.
Stem color: Near 137B.

FOLIAGE

Leaf:
- *Arrangement.*—Alternate single.
- *Average length.*—Approximately 4 cm.
- *Average width.*—Approximately 2.4 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Color.*—Young foliage upper side: Near 137A. Young foliage under side: Near 137C. Mature foliage upper side: Near 137A. Mature foliage under side: Near 137C. Venation upper side: Near 146A. Venation under side: Near 146B.

Petiole:
- *Average length.*—Approximately 1.5 cm.
- *Petiole color.*—Approximately 137A.

BLOOM

Inflorescence:
- *Flowering habit.*—Induced by darkness period greater than 13.5 hours, approximately 49 days of appropriate day length required to induce and develop blooms.
- *Inflorescence form: Daisy.*
- *Natural flowering season.*—Approximately mid-September.
- *Number of inflorescences per stem.*—Approximately 15 to 20.
- *Inflorescence diameter.*—Approximately 3.2 cm.
- *Inflorescence depth.*—Approximately 1.3 cm.
- *Disc diameter.*—Approximately 1 cm.
- *Inflorescence longevity on plant.*—Approximately 26–29 days.
- *Persistence.*—Persistent.
- *Fragrance.*—Not present.

Ray florets:
- *Appearance.*—Matte.
- *Texture.*—Smooth.
- *Average number per flower.*—Approximately 60 to 70.
- *Shape.*—Cylindric.
- *Margin.*—Entire.
- *Apex.*—Obtuse.
- *Length.*—Approximately 1.1 cm.
- *Color.*—Upper surface at first opening: on 20% nearest base: Near 13B. Upper surface at first opening: on 80% nearest apex: Near 46A. Upper surface at maturity: on 30% nearest base: Near 13B. Upper surface at maturity: on 70% nearest apex: Near 46A. Upper surface at fading: on 40% nearest base: Near 13B. Upper surface at fading: on 60% nearest apex: Near 46A. Under surface at first opening: on 20% nearest base: Near 13B. Under surface at first opening: on 80% nearest apex: Near 46A. Under surface at maturity: on 30% nearest base: Near 13B. Under surface at maturity: on 70% nearest apex: Near 46A. Under surface at fading: on 40% nearest base: Near 13B. Under surface at fading: on 60% nearest apex: Near 46A.

Disc florets:
- *Appearance.*—Shiny.
- *Texture.*—Smooth.
- *Average number per flower.*—Approximately 80 to 90.
- *Shape.*—Cylindric.
- *Apex.*—Obtuse.
- *Average length.*—Approximately 0.4 cm.
- *Average width.*—Approximately 0.1 cm.
- *Color.*—At first opening: Near 15A. At maturity: Near 15A. At fading: Near 15A.

Peduncle:
- *Length.*—At terminal end (shortest): Approximately 2.2 cm. At lateral end (longest): Approximately 4.3 cm.
- *Strength.*—Moderate.
- *Color.*—Near 137C.
- *Habit.*—Erect.

Inflorescence bud:
- *Length.*—Approximately 0.4 cm.
- *Diameter.*—Approximately 0.5 cm.
- *Form.*—Globular.
- *Color.*—Near 137B.

Sepals:
- *Appearance.*—Matte.
- *Texture.*—Lightly pubescent.
- *Number.*—Approximately 20 to 30.
- *Shape.*—Ovate.
- *Margin.*—Entire.
- *Apex.*—Acute.
- *Color.*—Upper side: Near 137C. Under side: Near 137C.

REPRODUCTIVE ORGANS

Ray florets:

*Number of pistils per floret.*—1.

*Stigma shape.*—2 branched.

*Stigma color.*—Near 15A.

*Stigma length.*—Approximately 0.1 cm.

*Style length.*—Approximately 0.3 cm.

*Number of stamens per floret.*—Absent.

Disc florets:

*Number of pistils per floret.*—1.

*Stigma shape.*—Cylindric.

*Stigma color.*—Approximately 1C.

*Style color.*—Approximately 154D.

*Number of stamens perfloret.*—Approximately 5.

*Anther shape.*—Tubular.

*Anther color.*—Near 15A.

*Pollen color.*—Near 15A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct variety of Chrysanthemum plant named 'MOZA BN 01' as herein illustrated and described.

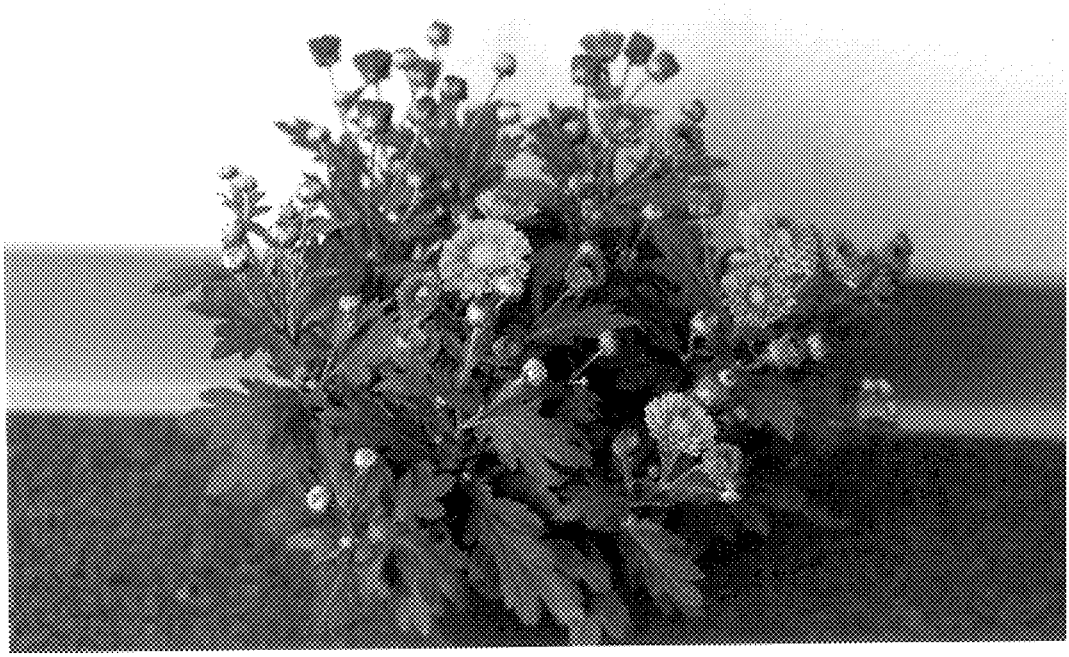

* * * * *